United States Patent
Nakao et al.

(10) Patent No.: US 9,295,436 B2
(45) Date of Patent: Mar. 29, 2016

(54) METHOD FOR MANUFACTURING INTRAORAL SENSOR

(71) Applicant: HAMAMATSU PHOTONICS K.K., Hamamatsu-shi, Shizuoka (JP)

(72) Inventors: Keisuke Nakao, Hamamatsu (JP); Kazuhisa Miyaguchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 123 days.

(21) Appl. No.: 13/911,520

(22) Filed: Jun. 6, 2013

(65) Prior Publication Data
US 2014/0360012 A1 Dec. 11, 2014

(51) Int. Cl.
*A61B 6/14* (2006.01)
*A61B 6/00* (2006.01)

(52) U.S. Cl.
CPC .................. *A61B 6/145* (2013.01); *A61B 6/425* (2013.01); *Y10T 29/49117* (2015.01)

(58) Field of Classification Search
CPC .......... A61B 5/00; A61B 6/145; A61B 6/425; Y10T 29/49117
USPC ....................................................... 29/592.1
See application file for complete search history.

(56) References Cited

U.S. PATENT DOCUMENTS

| | | | | |
|---|---|---|---|---|
| 6,030,119 | A * | 2/2000 | Tachibana et al. | 378/169 |
| 6,568,863 | B2 * | 5/2003 | Murata | 385/89 |
| 6,652,141 | B1 * | 11/2003 | Cianciosi | 378/191 |
| 2002/0061173 | A1 * | 5/2002 | Murata | 385/89 |
| 2007/0114547 | A1 * | 5/2007 | Fujita et al. | 257/98 |

FOREIGN PATENT DOCUMENTS

| | | |
|---|---|---|
| JP | H3-041411 | 4/1991 |
| JP | 08280669 A * | 10/1996 |
| JP | H9-045399 | 2/1997 |
| JP | 2009095464 A | 5/2009 |
| JP | 2010-524532 A | 7/2010 |
| JP | 2010-525563 A | 7/2010 |
| WO | WO 96/32064 | 10/1996 |
| WO | WO 2009/016916 | 2/2009 |

\* cited by examiner

*Primary Examiner* — Carl Arbes
(74) *Attorney, Agent, or Firm* — Drinker Biddle & Reath LLP

(57) ABSTRACT

A method for manufacturing an intraoral sensor having improved airtightness within its package is provided. A method for manufacturing this intraoral sensor comprises a first step S1 of arranging the signal cable 2 in a first mold, then filling the first mold with a first resin, and heating the first mold, so as to mold the cable connection unit 14 having the jacket 2c of the signal cable 2 welded thereto; a second step S2 of preparing the joint 13; a third step S3 of arranging the cable connection unit 14 at a predetermined position in the joint 13 by using a second mold; and a fourth step S4 of resin-sealing the joint 13 and cable connection unit 14 onto each other.

5 Claims, 8 Drawing Sheets

Fig.5
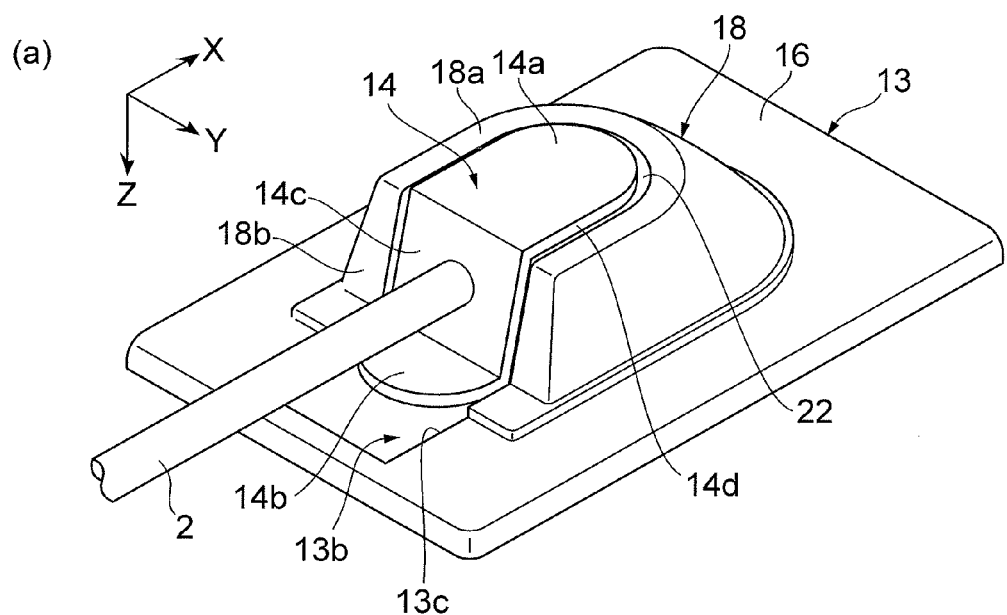
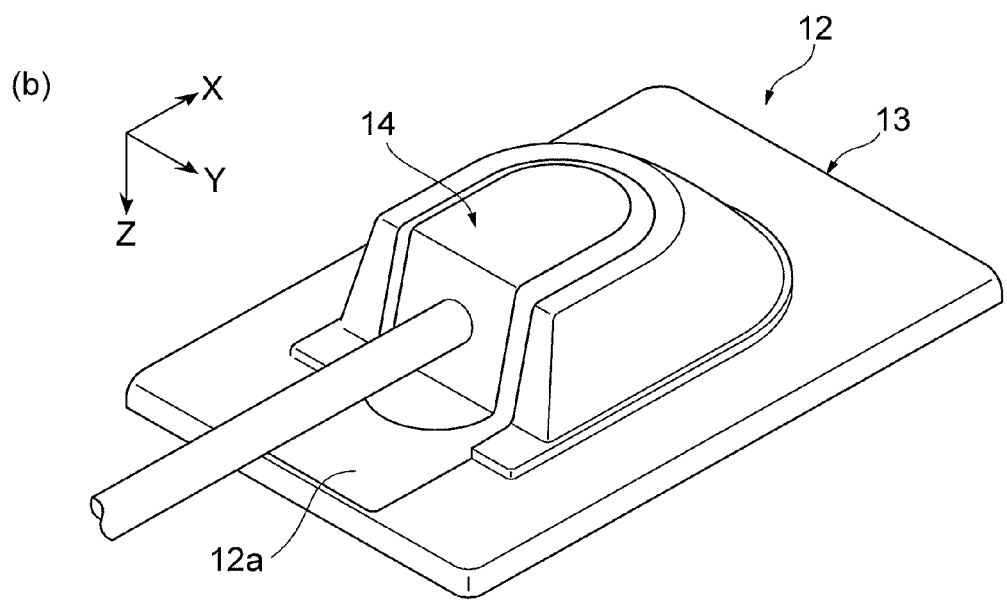

METHOD FOR MANUFACTURING INTRAORAL SENSOR

TECHNICAL FIELD

The present invention relates to a method for manufacturing an intraoral sensor which is inserted into an intraoral cavity.

BACKGROUND

Patent Literature 1 describes an imaging sensor which is inserted into an intraoral cavity and captures images of teeth and the like. The sensor described in Patent Literature 1 has a circuit board including an imaging device, a sensor body containing the circuit board and the like, and a cable electrically connected to the circuit board. The cable is secured to a cable connector provided with the sensor body.

Patent Literatures 1 and 2 are U.S. Pat. No. 6,652,141 and Japanese Patent Application Laid-Open No. 2009-95464, respectively.

SUMMARY

Intraoral sensors, which are inserted into intraoral cavities, may be disinfected each time when used. An example of methods for disinfecting the imaging sensor is wiping the sensor body with cloth impregnated with isopropyl alcohol. Dipping the sensor body in a disinfectant can surely disinfect it while being easier to perform than the method mentioned above.

In a structure such as that of the imaging sensor described in Patent Literature 1, however, the cable is secured to the sensor body with a bonding material (which will also be referred to as "securing by bonding" hereinafter) in general. The cable may bend at the part secured to the sensor body, thereby causing a stress. This stress may damage the bonding material itself and lower airtightness.

It is an object of the present invention to provide a method for manufacturing an intraoral sensor having improved airtightness within its package.

According to one aspect of the present invention, there is provided a method for manufacturing an intraoral sensor comprising an imaging device, a signal cable including a jacket, and a package for containing the imaging device, the package having a case for containing the imaging device and a cover for covering an opening of the case, the cover having a cable connection unit for connecting the signal cable and a joint for joining the cable connection unit to the case. The method comprises a first step of arranging the signal cable in a first mold, then filling the first mold with a first resin, and heating the first mold, so as to mold the cable connection unit having the jacket of the signal cable welded thereto; a second step of preparing the joint; a third step of arranging the cable connection unit at a predetermined position in the joint by using a second mold; and a fourth step of resin-sealing the joint and cable connection unit onto each other.

In the above-mentioned method, the jacket of the signal cable is secured to the cable connection unit by welding (which will also be referred to as "securing by welding" hereinafter). Hence, the gap between the jacket of the signal cable and the cable connection unit is buried surely. Even when a stress acts on the part where the signal cable and cable connection unit are secured to each other, the securing by welding inhibits the connection unit from being damaged. Therefore, an intraoral sensor having improved the airtightness of its package can be manufactured.

The first step may directly weld the first resin to the jacket, while molding the cable connection unit with the first resin. This first step welds the jacket 2c of the signal cable 2 to the cable connection unit simultaneously with forming the cable connection unit, whereby the jacket 2c of the signal cable 2 and the cable connection unit 14 can be formed more integrally.

The first step may comprise the steps of preparing the cable connection unit; arranging the signal cable and cable connection unit in the first mold; and filling the first mold with the first resin and arranging and heating the first resin between the cable connection unit and signal cable, so as to weld the first resin to the jacket of the signal cable and the cable connection unit. This first step does not weld the jacket of the signal cable and the cable connection unit directly to each other but secures the signal cable to the cable connection unit through the first resin. Therefore, even when the jacket of the signal cable cannot directly be welded to the cable connection unit, the signal cable can be secured to the cable connection unit, so as to manufacture an intraoral sensor having improved the airtightness of the package.

The method may further comprise a fifth step of electrically connecting the signal cable to the imaging device and arranging the imaging device in the case after the fourth step and a sixth step of securing the cover to the opening of the case after the fifth step. The fifth and sixth steps make it possible to manufacture an intraoral sensor having improved the airtightness of the package.

The sixth step may secure the case and cover to each other by bonding. This sixth step can easily secure the case and cover to each other.

A method for manufacturing an intraoral sensor having improved airtightness within the package can be provided as in the foregoing.

BRIEF DESCRIPTION OF DRAWINGS

FIG. 5 is a diagram for explaining a part of the manufacturing steps of the intraoral sensor in accordance with the first embodiment;

DESCRIPTION OF EMBODIMENTS

Figure 1:
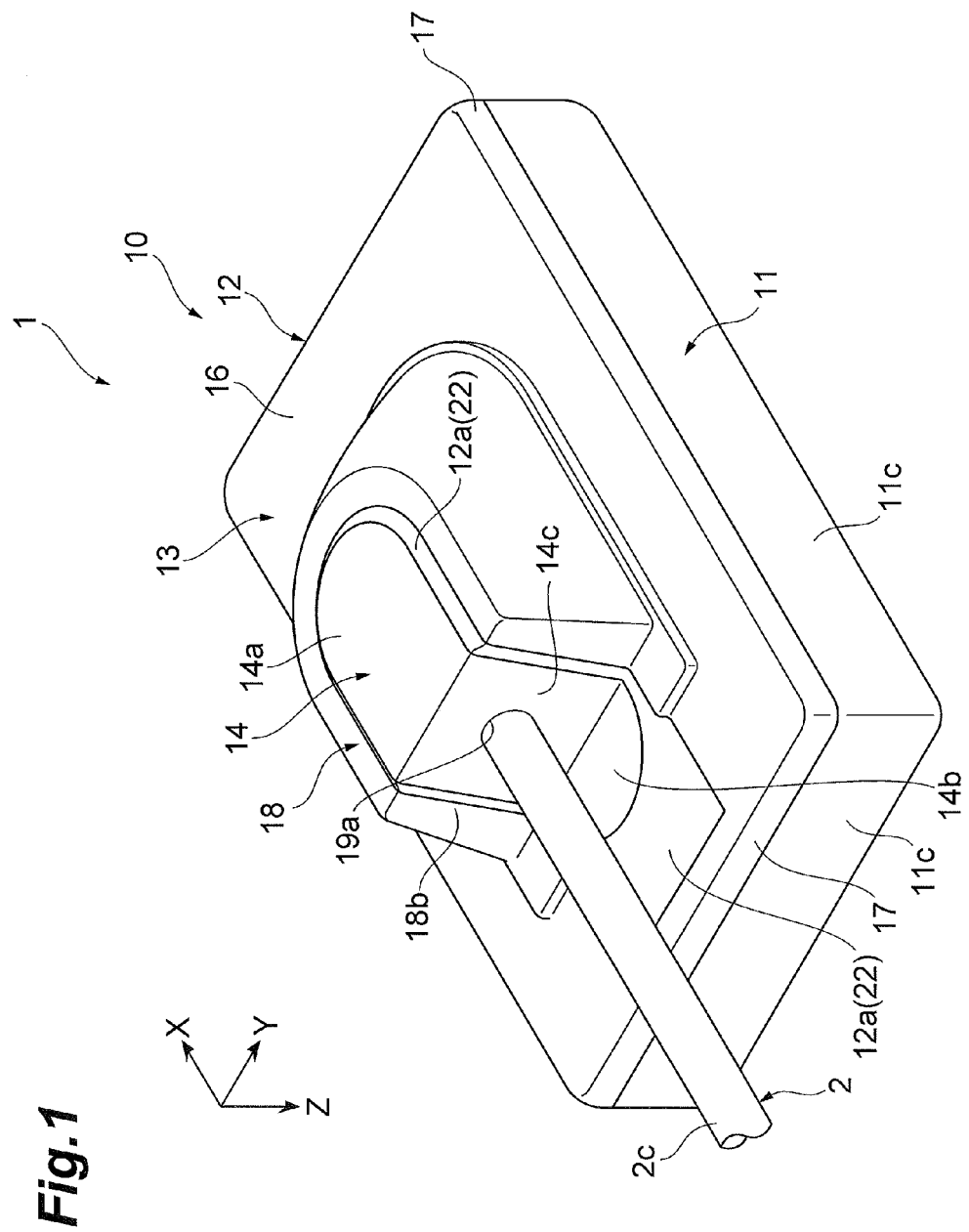
FIG. 1 is a diagram illustrating the exterior of the intraoral sensor in accordance with a first embodiment.

In the following, an embodiment of the method for manufacturing an intraoral sensor in accordance with one aspect of the present invention will be explained in detail with reference to the accompanying drawings. In the explanation of the drawings, the same constituents will be referred to with the same signs while omitting their overlapping descriptions. A three-dimensional orthogonal coordinate system will be set in the drawings and referred to when necessary in the following explanations. Here, X, Y, and Z axes will indicate the longitudinal, lateral, and thickness directions of a package 10, respectively.

First Embodiment

Figure 2:
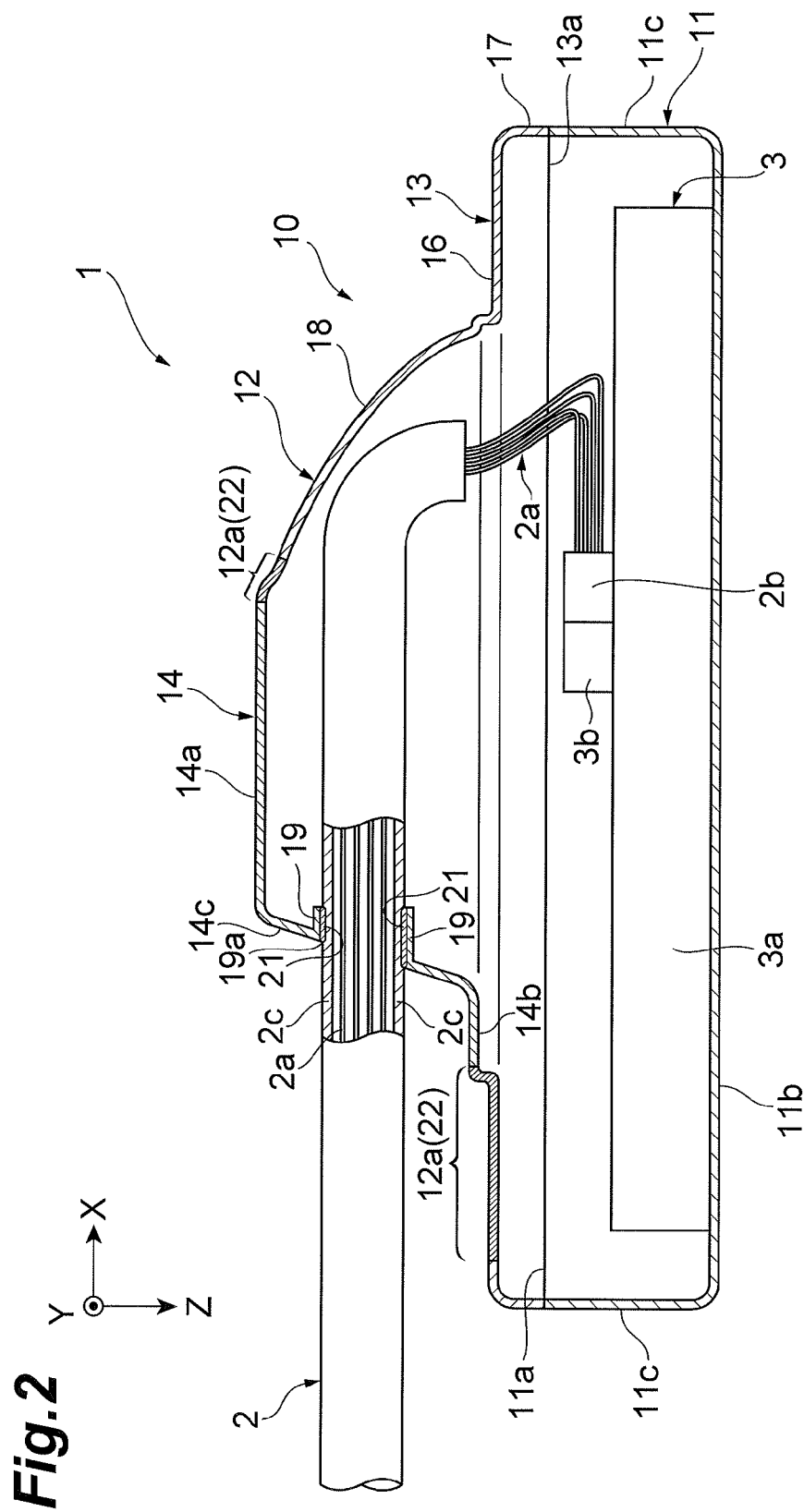
FIG. 2 is a diagram illustrating a cross-sectional structure of the intraoral sensor in accordance with the first embodiment.

An intraoral sensor manufactured by the method in accordance with the first embodiment will be explained. The intraoral sensor is a sensor, inserted into an intraoral cavity of a patient, for capturing X-ray images of teeth and the like in the intraoral cavity. As illustrated in FIGS. 1 and 2, this intraoral sensor 1 comprises a signal cable 2, an imaging device 3, and the package 10. The signal cable 2 is secured to the package 10. The imaging device 3 is arranged within the package 10.

The signal cable 2 has one end connected to the imaging device 3 and the other end connected to an external controller for controlling the intraoral sensor 1. The signal cable 2 comprises a plurality of wires 2a for transmitting predetermined electric signals, a connector 2b arranged at one end of the wires 2a, and a jacket 2c arranged about the plurality of wires 2a. The jacket 2c is made of polyvinyl chloride (PVC), for example.

The imaging device 3 comprises a photodetection element for converting an X-ray image into an electric image signal, a circuit board 3a for processing the output signal of the photodetection element, and a connector 3b disposed on the circuit board 3a. The connector 2b of the signal cable 2 is connected to the connector 3b.

The package 10 of the intraoral sensor 1 comprises a case 11 and a cover 12. The package 10 has a sealed/waterproof structure having improved airtightness.

The case 11 is a member for containing the imaging device 3. The case 11 is a rectangular parallelepiped boxy member having a rectangular opening 11a. The case 11 is made of acrylonitrile-butadiene-styrene copolymer synthetic resin (ABS), for example. The case 11 comprises a bottom 11b and a side wall 11c. The side wall 11c extends upward from the peripheral edges of the bottom 11b so as to define with the bottom 11b a container for containing the imaging device 3.

The cover 12 is a member for covering the opening 11a of the case 11. The cover 12 has a joint 13 and a cable connection unit 14. The cover 12 has a sealer 12a between the joint 13 and cable connection unit 14. The sealer 12a is a resin filling a gap (corresponding to 22 in part (a) of FIG. 5) formed between the joint 13 and cable connection unit 14. The resin is made of ABS containing polybutylene terephthalate (PBT), for example.

The joint 13, which is a member for joining the cable connection unit 14 to the case 11, is made of PBT-containing ABS, for example. The joint 13 has a rectangular parallelepiped member 16 having a rectangular opening 13a and a projection 18. The member 16 has a side wall 17. The side wall 17 extends from the peripheral edges of the member 16 toward the case 11. An end part of the side wall 17 on the opening 11a side abuts an end part of the side wall 11c of the case 11 on the opening 11a side and is secured thereto by a bonding material (securing by bonding). The projection 18 projecting away from the case 11 and cover 13 (in the negative Z direction) is disposed on the member 16 of the joint 13. The cable connection unit 14 is arranged in the projection 18.

The cable connection unit 14, which is a member for connecting the signal cable 2 to the package 10, is made of PBT-containing ABS, for example. The cable connection unit 14 comprises a first part 14a extending in the X direction, a second part 14b extending in the X direction while being separated from the first part 14a in the Z direction, and a third part 14c extending between the first and second parts 14a, 14b.

The cable connection unit 14 also has a cable fixer 19 formed in the third part 14c. The cable fixer 19 defines an opening 19a provided in the third part 14c. The signal cable 2 is inserted in the opening 19a, while the cable fixer 19 is disposed about the signal cable 2. The jacket 2c of the signal cable 2 is welded to the cable fixer 19. A weld part 21 is formed between the cable fixer 19 and jacket 2c. The weld part 21 secures the cable fixer 19 and jacket 2c to each other.

The weld part 21 is constituted by a resin which is formed by mixing PBT-containing ABS with PVC under heat. In the weld part 21, the composition of the resin continuously changes along a direction from the vicinity of the jacket 2c to the cable fixer 19. That is, the mixing ratio of the PBT-containing ABS and PVC continuously changes in the weld part 21. This makes it difficult to see the interface at which the jacket 2c and cable fixer 19 are joined to each other. In the opening 19a, the cable fixer 19 and jacket 2c are sealed onto each other with the weld part 21.

Figure 3:
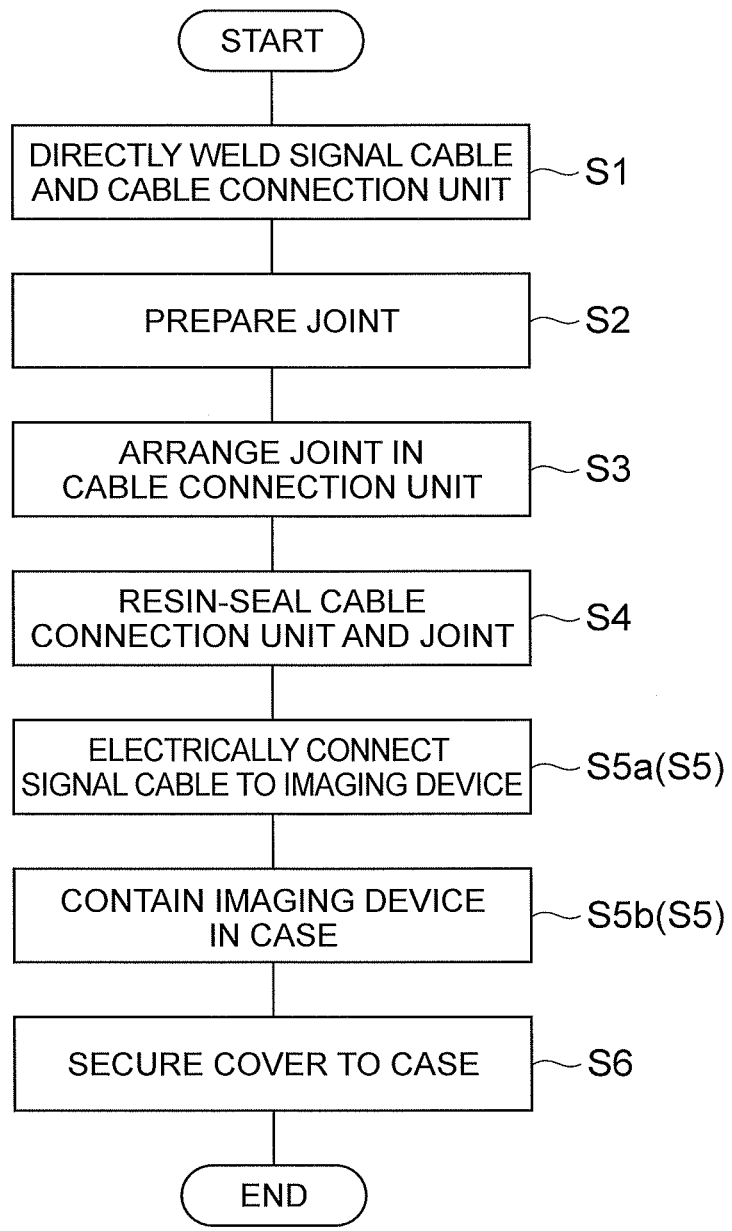
FIG. 3 is a flowchart illustrating steps of manufacturing the intraoral sensor in accordance with the first embodiment.
Figure 4:
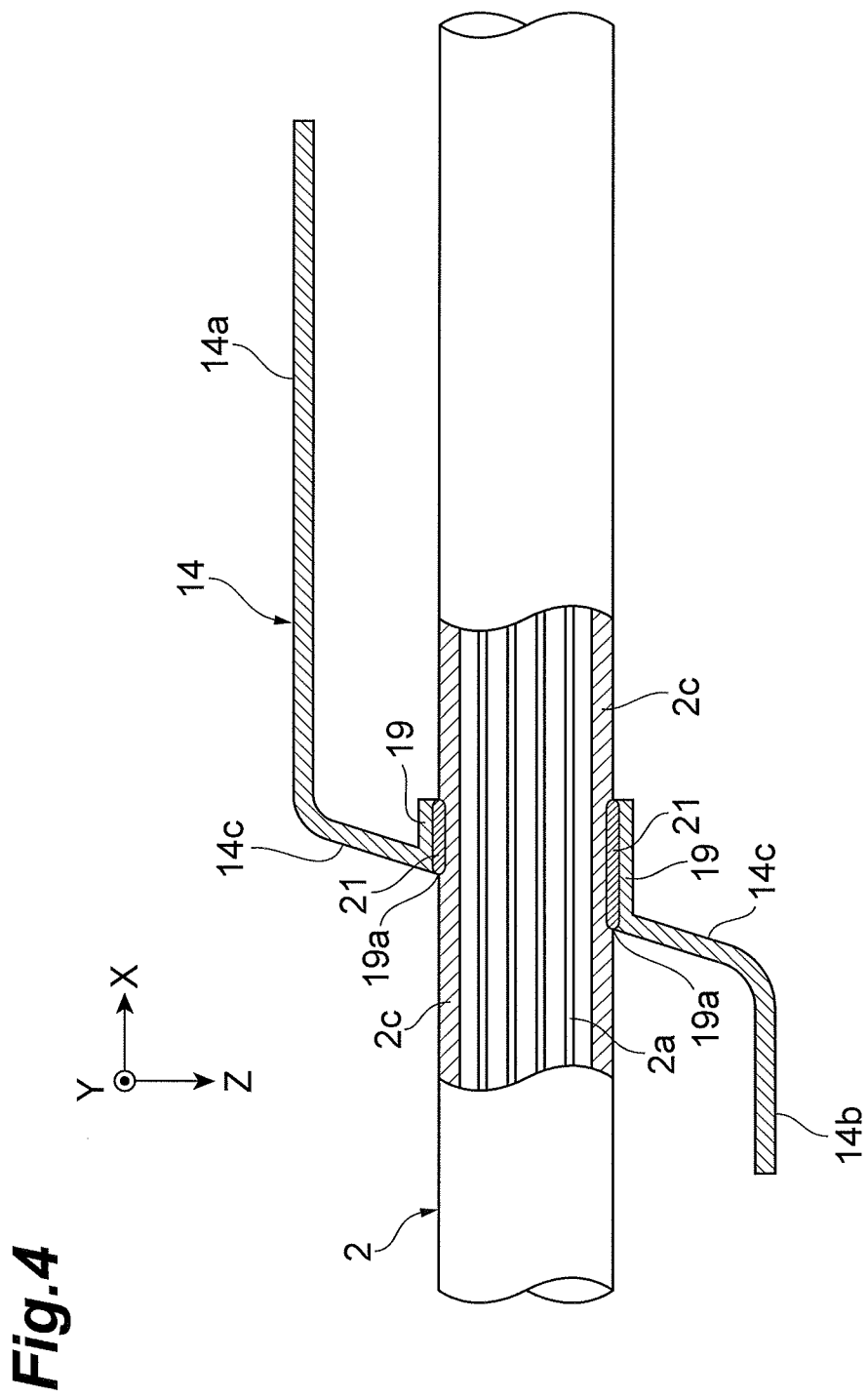
FIG. 4 is a diagram for explaining a part of the manufacturing steps of the intraoral sensor in accordance with the first embodiment.
Figure 6:
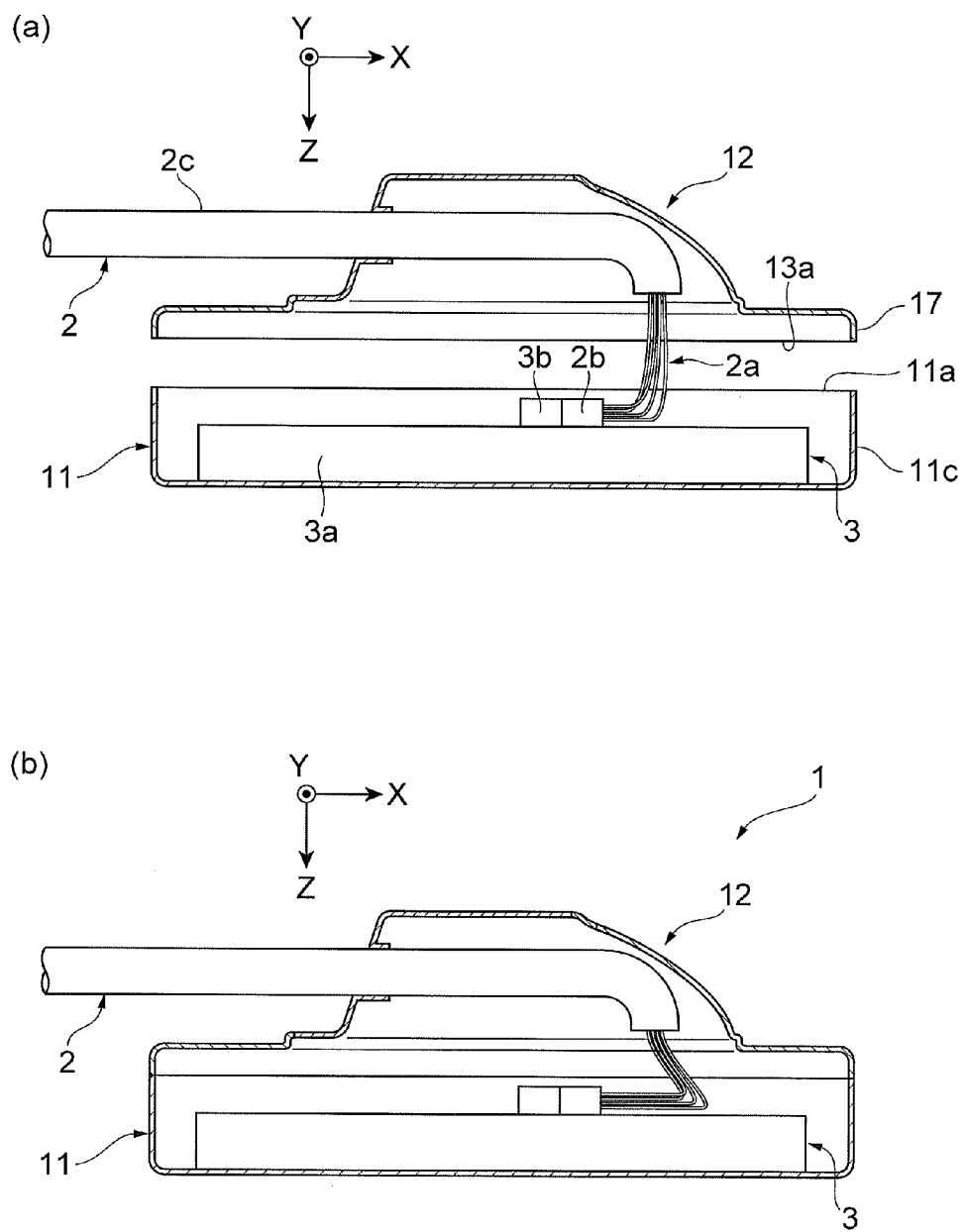
FIG. 6 is a diagram for explaining a part of the manufacturing steps of the intraoral sensor in accordance with the first embodiment.

A method for manufacturing the intraoral sensor 1 will now be explained with reference to FIGS. 3, 4, 5, and 6. FIG. 3 is a flowchart illustrating steps of manufacturing the intraoral sensor in accordance with the first embodiment. FIGS. 4, 5, and 6 are diagrams illustrating parts of the manufacturing steps of the intraoral sensor in accordance with the first embodiment.

First Step S1

The first step S1 molds the cable connection unit 14 to which the jacket 2c of the signal cable 2 is directly welded. More specifically, this first step S1 molds the cable connection unit 14 and welds the jacket 2c to the cable connection unit 14 at the same time. A first mold (not depicted) is prepared. The first mold is a mold for molding the cable connection unit 14. Subsequently, the signal cable 2 is arranged in the first mold. Then, the first mold is filled with a first resin. The first resin in this embodiment is an exterior molding resin for molding the cable connection unit 14, an example of which is PBT-containing ABS. Examples of a resin having such a structure include NOVALLOY B series (B14M0), manufactured by Daicel Polymer Ltd., containing PBT and ABS as main components. Thereafter, in a region where the cable fixer 19 and the jacket 2c are in contact with each other, the first mold filled with the first resin is heated until PBT-containing ABS constituting the cable fixer 19 and PVC constituting the jacket 2c melt into a mixture. Heating the first mold produces an area where PBT-containing ABS constituting the cable fixer 19 and PVC constituting the jacket 2c melt into a mixture in a region where the cable fixer 19 and the jacket 2c are in contact with each other. Then, the first mold is cooled. Cooling the first mold solidifies the first resin filling the first mold, thereby molding the cable connection unit 14. Simultaneously with molding the cable connection unit 14, the area where PBT-containing ABS and PVC are mixed, which is produced between the cable fixer 19 and jacket 2c, is solidified, whereby the weld part 21 is formed. As in the foregoing, the first step S1 molds the cable connection unit 14 to which the signal cable 2 is directly welded.

Second Step S2

The second step S2 prepares the joint 13. As with the cable connection unit 14, the joint 13 is made of PBT-containing ABS, which is an example of exterior molding resins. The joint 13 may be molded by filling a mold with a resin made of PBT-containing ABS at this point. The joint 13 that has been produced beforehand may also be used. The joint 13 is provided with an opening 13b for attaching the cable connection unit 14 to the joint 13 (see part (a) of FIG. 5). The opening 13b is formed in conformity to the shape of the cable connection unit 14.

Third Step S3

The third step S3 arranges the cable connection unit 14 in the opening 13b of the joint 13 (at a predetermined position) by using a second mold (not depicted). When the joint 13 and cable connection unit 14 are arranged in the second mold, a gap 22 is formed between a peripheral wall 13c defining the opening 13b of the joint 13 and a peripheral wall 14d of the cable connection unit 14 (see part (a) of FIG. 5).

Fourth Step S4

The fourth step S4 seals the gap 22 between the joint 13 and cable connection unit 14 with a resin. The fourth step S4 molds the cover 12. First, the second mold is filled with a second resin. As the second resin, PBT-containing ABS, which is an example of exterior molding resins, can be used, for instance. Filling the second mold with the second resin allows the latter to cover and bury the gap 22. Subsequently, the second mold is heated until PBT-containing ABS constituting each of the joint 13, cable connection unit 14, and second resin is melted. Then, the second mold is cooled. Cooling the second mold solidifies PBT-containing ABS, thereby forming the sealer 12a. After the second resin is solidified, the cover 12 is taken out of the second mold. As in the foregoing, the third and fourth steps S3 and S4 mold the cover 12 in which the cable connection unit 14 and joint 13 are integrated with each other.

Fifth Step S5

The fifth step S5 will now be explained. The fifth step S5 electrically connects the signal cable 2 to the imaging device 3 (S5a) and then arranges the imaging device 3 in the case 11 (S5b).

Sixth Step S6

The sixth step S6 secures the cover 12 to the case 11. First, a bonding material is applied to an end face of the side wall 17 of the cover 12 or an end face of the side wall 11c of the case 11. Subsequently, as illustrated in part (b) of FIG. 6, the cover 12 is attached to the case 11 under pressure, whereby the cover 12 is secured to the case 11 through the bonding material (securing by bonding). As the bonding material, an epoxy-resin-based adhesive or silicone-based adhesive can be used, for example. The foregoing steps S1 to S6 manufacture the intraoral sensor 1 in which the signal cable 2 and package 10 are integrated with each other.

The method for manufacturing the intraoral sensor in accordance with this embodiment secures the jacket 2c of the signal cable 2 to the cable fixer 19 of the cable connection unit 14 through the weld part 21. This can surely fill the gap between the jacket 2c of the signal cable 2 and the cable fixer 19. It also inhibits stresses from damaging the junction between the signal cable 2 and cable fixer 19. Hence, the intraoral sensor 1 having improved the airtightness of the package 10 can be manufactured.

The first step S1 welds the signal cable 2 to the cable connection unit 14 simultaneously with forming the cable connection unit 14, whereby the jacket 2c of the signal cable 2 and the cable connection unit 14 can be formed more integrally with each other.

EXAMPLE 1

A leak test for seeing the airtightness of the intraoral sensor 1 was performed. This test dipped the intraoral sensor 1 in water, fed air into the package 10 through the inside of the signal cable 2, and saw whether or not the air leaked from the inside of the package 10 to the outside thereof. The air having a predetermined pressure was fed into the package 10.

First, an intraoral sensor manufactured by a conventional manufacturing method was prepared. The conventional intraoral sensor differed from the intraoral sensor 1 in that the signal cable and cable connection unit were secured to each other by a bonding material (securing by bonding) and that the cable connection unit and joint were secured by bonding. It also differed from the intraoral sensor 1 in that each of its case, joint, and cable connection unit was molded with ABS.

The conventional intraoral sensor was dipped in water, and the air was fed into the package through the inside of the signal cable. At the air pressure of 0.02 MPa, a bubble occurred from between the signal cable and cable connection unit, whereby the air was visually seen to leak.

In the intraoral sensor 1, on the other hand, it was seen that no air leaked from the package 10 even at the air pressures of 0.1 MPa, 0.12 MPa, and 0.15 MPa. Hence, the intraoral sensor 1 was seen to improve airtightness over the conventional intraoral sensor.

This result corresponds to an IP67 test. The IP code is a standard for protection of electric equipment and the like against solid foreign matters and water. A test based on the IP67 standard sees that no dust enters the inside of electric equipment and that it is not adversely affected even when immersed in water under defined conditions of pressure and time. Specifically, in a test conforming to the IP67 standard, electric equipment is immersed in water at a depth of 1 m for 30 min, and whether or not there is ingress of water is seen. In the conditions of Example 1, the case where the air was fed into the package 10 at the pressure of 0.1 MPa corresponds to the test. Hence, it could be seen that the intraoral sensor 1 manufactured by the method in accordance with the first embodiment had the airtightness corresponding to the IP67.

EXAMPLE 2

Another leak test for seeing the airtightness of the intraoral sensor 1 was performed. This test dipped the intraoral sensor 1 for 30 days in a tank of water having a depth of several centimeters. As a result, it was seen that no water entered the inside of the package 10 of the intraoral sensor 1. This verified that the intraoral sensor 1 manufactured by the method in accordance with the first embodiment had sufficient airtightness.

Second Embodiment

Figure 7:
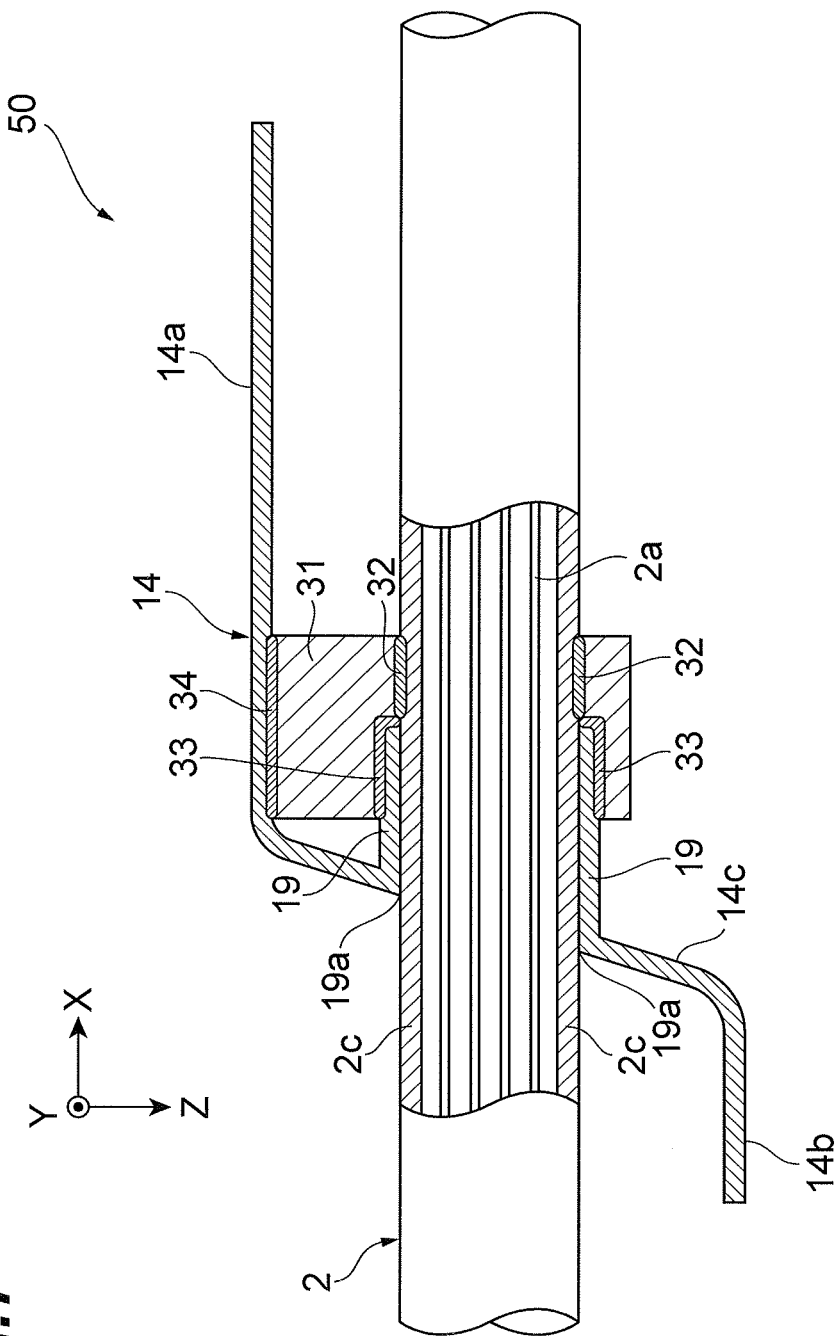
FIG. 7 is a diagram illustrating a partly cross-sectional structure of the intraoral sensor in accordance with a second embodiment.

First, an intraoral sensor 50 in accordance with the second embodiment will be explained. FIG. 7 is a diagram partly illustrating the structure of the intraoral sensor 50. The intraoral sensor 50 differs from the intraoral sensor 1 in that it has a resin part 31 made of a first resin.

The resin part 31 is made of a resin mainly composed of PBT. The resin part 31 has first, second, and third weld parts 32, 33, 34.

The first weld part 32 is made of a resin formed between the cable fixer 19 and resin part 31, which is a mixture of PVC constituting the jacket 2c and PBT constituting the resin part 31. In this resin, the mixing ratio of PVC and PBT continuously changes along a direction from the jacket 2c to the resin part 31.

The second weld part 33 is made of a resin formed between the cable fixer 19 and resin part 31, which is a mixture of ABS constituting the cable fixer 19 and PBT constituting the resin part 31. In this resin, the mixing ratio of ABS and PBT continuously changes along a direction from the cable fixer 19 to the resin part 31.

The third weld part 34 is made of a resin formed between the first part 14a of the cable connection unit 14 and the resin part 31, which is a mixture of ABS constituting the cable connection unit 14 and PBT constituting the resin part 31. In this resin, the mixing ratio of ABS and PBT continuously changes along a direction from the cable connection unit 14 to the resin part 31.

Forming the first, second, and third weld parts 32, 33, 34 surely seals the signal cable 2 and cable connection unit 14 onto each other. In such a structure, the jacket 2c of the signal cable 2 and the cable connection unit 14 are not directly welded to each other, but the resin part 31 is welded to the jacket 2c and cable connection unit 19, whereby the signal cable 2 and cable connection unit 14 are sealed onto each other.

Figure 8:
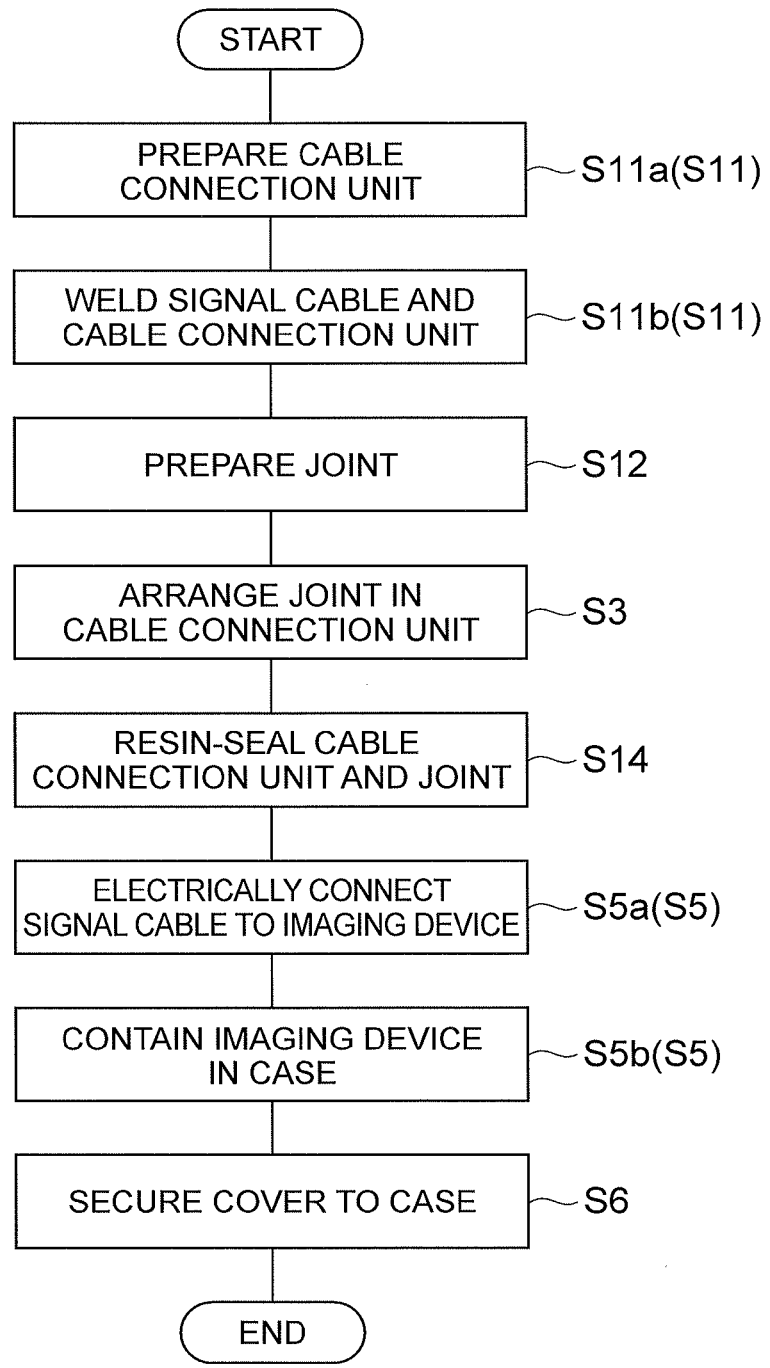
FIG. 8 is a flowchart illustrating steps of manufacturing the intraoral sensor in accordance with the second embodiment.

A method for manufacturing the intraoral sensor 1 in accordance with the second embodiment will now be explained. FIG. 8 is a flowchart illustrating steps of manufacturing the intraoral sensor in accordance with the second embodiment. In the method of the second embodiment, its first step S11 differs from the first step S1 of the method of the first embodiment in that it has a step S11a of preparing the cable connection unit 14 and a step S11b of welding the first resin to the jacket of the signal cable and the cable connection unit.

The material molding the joint 13 in the second step S12 differs from that used in the second step S2 of the method of the first embodiment. The material filling the gap between the cable connection unit 14 and joint 13 in the fourth step S14 differs from that used in the fourth step S4 of the method of the first embodiment.

Steps similar to the third, fifth, and sixth steps S3, S5, S6 of the method in accordance with the second embodiment are also used in the method in accordance with the first embodiment. In the following, the first, second, and fourth steps S11, S12, S14 will be explained in detail.

First Step S11

The first step S11 has the step S11a of preparing the cable connection unit 14 and the step S11b of securing the signal cable 2 to the cable connection unit 14 through the first resin.

First, the cable connection unit 14 is prepared. The cable connection unit 14 is molded by filling a predetermined mold with an exterior molding resin. For example, ABS may be used as the exterior molding resin. As such a resin, DENKA ABS QF-T, manufactured by Denki Kagaku Kogyo K.K., containing ABS as a main component may be used, for example.

Next, a first mold is prepared, and the signal cable 2 and cable connection unit 14 are arranged therein. Subsequently, the first mold is filled with the first resin.

As the first resin in the second embodiment, PBT is used as an example of molding resins for welding. As such a molding resin for welding, DURANEX 353RA, manufactured by Polyplastics Co., Ltd., containing PBT as a main component, may be used, for example.

Next, the first mold filled with the first resin is heated until the jacket 2c and resin part 31 melt into a mixture in a region where they are in contact with each other, the cable fixer 19 and resin part 31 melt into a mixture in a region where they are in contact with each other, and the first part 14a of the cable connection unit 14 and the resin part 31 melt into a mixture in a region where they are in contact with each other. Heating the first mold produces an area where PVC and PBT melt into a mixture in a region where the jacket 2c and resin part 31 are in contact with each other. It also produces an area where ABS and PBT melt into a mixture in a region where the cable fixer 19 and resin part 31 are in contact with each other. It also produces an area where ABS and PBT melt into a mixture in a region where the cable connection unit 14 and resin part 31 are in contact with each other.

Then, the first mold is cooled. This solidifies the area where PVC and PBT melt into a mixture, produced between the jacket 2c and resin part 31, thereby forming the first weld part 32. It also solidifies the area where ABS and PBT melt into a mixture, produced between the cable fixer 19 and resin part 31, thereby forming the second weld part 33. It also solidifies the area where ABS and PBT melt into a mixture, produced between the cable connection unit 14 and resin part 31, thereby forming the third weld part 34. As in the foregoing, the first step S11 molds the cable connection unit 14 to which the signal cable 2 is welded.

Second Step S12

The second step S12 prepares the joint 13. The joint 13 used in the second step S12 is made of ABS, which is an example of exterior molding resins as with the cable connection unit 14.

Fourth Step S14

First, a second mold is filled with a second resin. For example, ABS can be used for the second resin. Filling the second mold with the second resin allows the latter to cover and bury the gap 22. Subsequently, the second mold is heated until ABS constituting each of the joint 13, cable connection unit 14, and second resin melts. Cooling the second mold solidifies the second resin covering the gap 22, thereby forming the sealer 12a.

The method for manufacturing the intraoral sensor of the second embodiment can manufacture the intraoral sensor 50 having improved the airtightness of the package 10 as with the method for manufacturing the intraoral sensor of the first embodiment. Further, the method for manufacturing the intraoral sensor of the second embodiment does not weld the jacket 2c of the signal cable 2 and the cable connection unit 14 directly to each other but secures the signal cable 2 to the cable connection unit 14 through the resin part 31. Therefore, even when the jacket 2c of the signal cable 2 cannot directly be welded to the cable fixer 19, the signal cable 2 can be secured to the cable fixer 19, so as to manufacture the intraoral sensor 50 having improved the airtightness of the package 10.

The above-mentioned first and second embodiments illustrate examples of the method for manufacturing an intraoral sensor in accordance with one aspect of the present invention. The method for manufacturing an intraoral sensor in accordance with one aspect of the present invention is not limited to the first and second embodiments. For example, the first and second resins and the resin constituting the jacket 2c may also be selected from resins other than those mentioned above.

For example, when PVC is chosen as a material for the jacket 2c of the signal cable 2 in the method in accordance with the first embodiment, various resins which can favorably be welded to PVC may be selected as the first resin. Examples of resins which can favorably be welded to PVC include ABS, polyamide 6 (PA6), polybutylene terephthalate (PBT), polyphenylene sulfide (PPS), polycarbonate (PC), polyarylate (PAR), and thermoplastic elastomers (TPE).

Crosslinking polyethylene may also be selected as a material for the jacket 2c of the signal cable 2. Examples of resins which can favorably come into close contact with crosslinking polyethylene include ABS, PA6, and PPS, which may be selected as the first resin.

Crosslinking polyurethane may also be selected as a material for the jacket 2c of the signal cable 2. Examples of resins which can favorably come into close contact with crosslinking polyurethane include ABS, PA6, PBT, PPS, and TPE, which may be selected as the first resin.

The method in accordance with the first embodiment may further comprise the step of forming the resin part 31 after the first step. Such a method can manufacture the intraoral sensor 1 having further improved the airtightness.

The case 11 and cover 12 may be secured to each other by welding. Such a structure can manufacture the intraoral sensors 1, 50 having further improved the airtightness in their packages.

The invention claimed is:

1. A method for manufacturing an intraoral sensor comprising an imaging device, a signal cable including a jacket, and a package for containing the imaging device, the package having a case for containing the imaging device and a cover for covering an opening of the case, the cover having a cable connection unit for connecting the signal cable and a joint for joining the cable connection unit to the case, the method comprising:

a first step of arranging the signal cable in a first mold, then filling the first mold with a first resin, and heating the first mold, so as to mold the cable connection unit having the jacket of the signal cable welded thereto;

a second step of preparing the joint;

a third step of arranging the cable connection unit at a predetermined position in the joint by using a second mold; and a fourth step of resin-sealing the joint and cable connection unit onto each other.

2. The method for manufacturing an intraoral sensor according to claim 1, wherein the first step directly welds the first resin to the jacket, while molding the cable connection unit with the first resin.

3. The method for manufacturing an intraoral sensor according to claim 1, wherein the first step comprises the steps of:

preparing the cable connection unit;

arranging the signal cable and cable connection unit in the first mold; and filling the first mold with the first resin and arranging and heating the first resin between the cable connection unit and signal cable, so as to weld the first resin to the jacket of the signal cable and the cable connection unit.

4. The method for manufacturing an intraoral sensor according to claim 1, further comprising:

a fifth step of electrically connecting the signal cable to the imaging device and arranging the imaging device in the case after the fourth step; and a sixth step of securing the cover to the opening of the case after the fifth step.

5. The method for manufacturing an intraoral sensor according to claim 4, wherein the sixth step secures the case and cover to each other by bonding.

* * * * *